US005665313A

United States Patent [19]

Shimada et al.

[11] Patent Number: 5,665,313
[45] Date of Patent: Sep. 9, 1997

[54] DETECTING AGENT

[75] Inventors: Takashi Shimada; Masako Yamakawa; Youji Nawa, all of Hiratsuka, Japan

[73] Assignee: Japan Pionics Co., Ltd., Tokyo, Japan

[21] Appl. No.: 511,681

[22] Filed: Aug. 7, 1995

[30] Foreign Application Priority Data

Sep. 5, 1994 [JP] Japan .................................. 6-234490

[51] Int. Cl.$^6$ .................................................. G01N 33/52
[52] U.S. Cl. ............................ 422/86; 422/61; 436/103; 436/164
[58] Field of Search ........................ 422/86, 61; 436/164, 436/103

[56] References Cited

U.S. PATENT DOCUMENTS

| | | | |
|---|---|---|---|
| 3,455,656 | 7/1969 | Roberts | 422/86 |
| 4,043,934 | 8/1977 | Shuler et al. | 252/186 |
| 4,532,120 | 7/1985 | Smith et al. | 436/103 |

FOREIGN PATENT DOCUMENTS

WO 88/05911  8/1988  WIPO.

OTHER PUBLICATIONS

Database WPI, Section Ch, Week 9011, Derwent Publications Ltd., London, Gb; Class A89, AN 90-079301 of JP-A-02 032 254, 2 Feb. 1990.
Patent Abstracts of Japan, vol. 14, No. 185 (P-1036), 13 Apr. 1990 of JP-A-02 032 254.
Database WPI, Section Ch, Week 9326, Derwent Publication Ltd., London, GB; Class E36, AN 93-211441 of JP-A-05 137 951, 1 Jun. 1993.
Patent Abstracts of Japan, vol. 17, No. 506 (C-110), 13 Sep. 1993, of JP-A-05 137 951.
Database WPI, Section Ch, Week 8710, Derwent Publications Ltd., GB; Class E36, AN 87-068238 of JP-A-62 021 061, 29 Jan. 1987.
Patent Abstracts of Japan, vol. 11, No. 197 (P-589), 25 Jun. 1987 of JP-A-62 021 061.
M. Colombier et al, "Use of phosphomolybdic acid in the determination of hydroborates", Chemical Abstracts, vol. 102, No. 6, 11 Feb. 1985, Columbus, Ohio, US, column 1, Analysis, vol. 12, No. 5, 1984, pp. 269-272.

*Primary Examiner*—Lyle A. Alexander
*Attorney, Agent, or Firm*—Frishauf, Holtz, Goodman, Langer & Chick, P.C.

[57] ABSTRACT

A detecting agent for hydride gases (arsine, phosphine, silane, diborane, selenium hydride etc.) which comprises at least one member selected from molybdic acid, a salt thereof, a molybdenum-containing acid (molybdophosphoric acid, etc.) and a salt thereof, and optionally a cupric salt each as a discoloring component being supported on an inorganic carrier (silica, alumina, silica-alumina, zirconia, etc.). The above detecting agent can detect the above hydride gases contained in the exhaust gas discharged from a semiconductor manufacturing process, with high accuracy, selectivity and sensitivity at a high discoloring rate without being influenced by other gases such as hydrogen gas.

15 Claims, No Drawings

DETECTING AGENT

BACKGROUND OF THE INVENTION

1. Field of the Invention

The present invention relates to a detecting agent. More particularly, it pertains to a detecting agent for a hydride gas contained in a gas which is used for chemical vapor deposition (CVD), ion implantation or the like in a semiconductor manufacturing process and then discharged from the process.

2. Description of the Related Arts

With the development of semiconductor industries, there has recently been a steady rise in the amounts of inflammable hydride gases such as arsine, phosphine, silane, diborane and selenium hydride that are used in the above-mentioned industries.

These hydride gases are indispensable each as a raw material gas or a doping gas for the production process of silicon semiconductors and compound semiconductors, but they are highly toxic. It is therefore, necessary in the handling of any of the foregoing hydride gases, to determine at all times whether or not the gas leaks out to the working environment, and in the event of a gas leakage to notify the workers of the leakage without fail and simultaneously take appropriate safety measures thereagainst.

In addition, the exhaust gas discharged from a semiconductor manufacturing process frequently contains some of the aforesaid hydride gases and thus, it is required to purify the exhaust gas by the use of a detoxifying apparatus, and at the same time, to confirm the sufficient removal of the hydride gases prior to the discharge of the exhaust gas.

It is well-known that the use of a detecting agent is effective for detecting a hydride gas. As a method for using a detecting agent for example, in the case of detecting a leakage of the hydride gas into a working environment, mention may be made of a method in which a gas taken in the working environment is passed through a detector tube made of a glass tube packed inside with a detecting agent, and a leakage, if any, is detected by the discoloration (that is, color change, as referred to hereinafter) of the detecting agent. In the case of detecting the breakthrough of a harmful gas (hydride gas) in a purifying column for the harmful gas, there is generally adopted a detection method in which an observation is made for a discoloration of a detecting agent packed in an observation port of the purifying column.

There have heretofore been known for example, as a detecting agent for hydride gases, a detecting agent for phosphine which comprises a mercuric salt or a mercuric complex salt alone or a mixture of the same and a ferric salt or a cupric salt along with a silica-gel carrier supporting any of the aforesaid salt (refer to Japanese patent publication No. 844/1948); and a detecting agent for arsine and phosphine which comprises gold chloride and mercuric chloride that are supported on a granular carrier (refer to U.S. Pat. No. 3,112,998).

However, the above-mentioned detecting agents involve the problems that the sensitivity is not necessarily sufficient and that delicate care must be taken in handling mercury (II) and a salt thereof because of their extremely high toxicity.

Moreover, in the case where there is contained, in a gas which is the object of detection, hydrogen gas which is employed as a carrier gas in a semiconductor manufacturing process or the like or hydrogen gas which is formed by the catalytic cracking of a purifying agent and a hydride gas at the time of discharge, the detecting agent is discolored by the aforesaid hydrogen, thus causing the problem that selective detection only of the hydride gas is made impossible thereby.

SUMMARY OF THE INVENTION

Under such circumstances, intensive research and investigation were accumulated by the present inventors in order to eliminate such disadvantages as involved in the prior arts and obtain a detecting agent for hydride gases which is safe in handling, high in sensitivity to hydride gases and free from discoloration due to a gas other than the hydride gases, such as hydrogen. As a result, it has been found that the subject can be attained by using a detecting agent comprising molybdic acid or a salt thereof as a discoloring component. The present invention has been accomplished by the above-mentioned finding and information.

Specifically the present invention provides a detecting agent for hydride gases which comprises at least molybdic acid or a salt thereof as a discoloring component which is supported on an inorganic carrier.

DESCRIPTION OF THE PREFERRED EMBODIMENT

The detecting agent according to the present invention is effective for the detection of a hydride gas such as arsine, phosphine, silane, diborane and selenium hydride each being contained in nitrogen, hydrogen, argon, helium, air or the like, and is favorably used for the detection of a hydride gas, especially arsine, phosphine and silane each being most commonly contained in an exhaust gas from a semiconductor manufacturing process.

When the foregoing detecting agent comes in contact with a hydride gas to be detected, the discoloring component sensitively discolors from lemon color or yellow, to bluish green or black.

With regard to molybdic acid or a salt thereof as a discoloring agent usable in the present invention, mention may be made of a variety of molybdic compounds. By the term "molybdic acid" as used herein is meant not only molybdic acid itself but also a molybdenum-containing inorganic acid or organic acid, specifically exemplified by molybdophosphoric acid (phosphomolybdic acid), molybdosilicic acid and molybdoboric acid. Likewise by the term "molybdate, namely salt of molybdic acid" is meant a salt of molybdic acid as well as a salt of a molybdenum-containing acid, which are specifically exemplified by an alkali metal salt (sodium salt and potassium salt), ammonium salt, etc. each of molybdic acid or molybdenum-containing acid. Of these, molybdophosphoric acid and its sodium salt, potassium salt and ammonium salt are preferable from the viewpoints of ease of availability and water-solubility. Other preferable examples include molybdic acid, its sodium salt, potassium salt and ammonium salt. The above-mentioned molybdic acid and a salt thereof encompass an anhydride and hydrates of each of them.

The amount of the molybdic acid or a salt thereof to be supported on an inorganic carrier may be suitably selected according to the situation, but is usually 1:0.00001 to 0.2, preferably 1:0.0002 to 0.05 expressed in terms of the ratio by weight of the inorganic carrier to the metallic molybdenum in the molybdic acid or a salt thereof.

The discoloring agent in the present invention can detect a hydride gas even when molybdic acid or a salt thereof is used alone as the agent, but it is preferable that the agent be incorporated with a cupric salt for the purpose of further enhancing the sensitivity and the discoloration rate.

As the usable cupric salt, mention may be made of a cupric salt of an inorganic acid and that of an organic acid. Examples of the cupric salt of an inorganic acid include a cupric salt of an oxoacid and a halogenated cupric salt. The cupric salt of an oxoacid is exemplified by a cupric salt of carbonic acid, silicic acid, nitric acid, sulfuric acid, arsenic acid, boric acid, chloric acid, perchloric acid, chlorous acid or hypochlorous acid. The halogenated cupric salt is exemplified by cupric chloride, cupric bromide and cupric iodide. Examples of the cupric salt of an organic acid include a cupric salt of an aliphatic monocarboxylic acid such as formic acid, acetic acid, propionic acid, oleic acid and stearic acid; an aliphatic dicarboxylic acid such as oxalic acid, adipic acid and sebacic acid; an oxy acid such as lactic acid and tartaric acid; an aromatic carboxylic acid such as benzoic acid and toluic acid; and a variety of acids such as naphthenic acid. Of these, cupric nitrate, cupric sulfate, cupric chloride, cupric bromide and cupric acetate are preferable from the viewpoints of water-solubility and ease of handling.

In the case where a cupric salt is used in combination with molybdic acid or a salt thereof each as a discoloring component, the amount of molybdic acid or a salt thereof and a cupric salt to be supported on the inorganic carrier varies depending upon the kind, concentration and the like of the hydride gas which is the object of detection and thus can not be unequivocally specified, but is usually 1:0.00001 to 0.1:0.00001 to 0.05, preferably 1:0.0002 to 0.02:0.0001 to 0.005, approximately, expressed in terms of the ratio by weight of the inorganic carrier:metallic molybdenum in the molybdic acid or a salt thereof:metallic copper in the cupric salt.

A proportion of metallic molybdenum less than 0.00001 leads to difficulty in identifying a discoloration, whereas that more than 0.1 results in failure to further enhance the sensitivity, thus causing increased costs and besides, brings about a fear of discoloring due hydrogen depending on the detection conditions. On the other hand, a proportion of metallic copper in excess of 0.05 also results in failure to further enhance the sensitivity and moreover brings about a fear of difficulty in identifying a discoloration because of increase in bluishness of the detecting agent itself.

The inorganic carrier to be used in the present invention is not specifically limited in its type insofar as the carrier is pale enough so as to enable the discoloring component supported thereon to be identified in discoloration. Examples of usable inorganic carriers include silica, silica-alumina, alumina, aluminosilicate, zirconia and the like and, as a preferable one, a catalyst carrier having a specific surface area of 50 to 1000 $m^2/g$, approximately. Of these, white to colorless silica and alumina are preferable and white to colorless silica-gel is particularly preferable.

The silica-gel which is available on the market as a desiccant and has a specific surface area of 450 to 800 $m^2/g$, approximately may be used in the present invention, but it is preferable to select specific silica-gel which is formed by means of hydrothermal synthesis or the like and has a specific surface area in the range of 50 to 500 $m^2/g$, approximately for the purpose of attaining the object of the present invention in a further advanced manner.

As a method for making the inorganic carrier support the discoloring agent, mention is made, for example, of a method in which the inorganic carrier is immersed in a solution or a suspension of the discoloring component in water or any of various organic solvents to support the agent; a method in which the above-mentioned solution or suspension is sprayed onto the surface of the carrier so that the agent is supported on the carrier; and the like methods.

The gas velocity at the time of the detecting agent being brought into contact with the gas to be detected is not specifically limited, but from the practical viewpoint it is usually 0.01 to 100 cm/sec in terms of linear space velocity in a semiconductor manufacturing apparatus and an exhaust gas treatment unit.

The temperature and pressure of the gas at the time of contact with the detecting agent are preferably in the range of $-20°$ to $300°$ C. and 0.001 to 20 $kg/cm^2$, respectively.

The detecting agent in the form of a solid according to the present invention is packed for use usually in a glassmade detecting tube, a transparent vessel made of a transparent plastics or a transparent observation port located on a gas purifying column. Thus, a hydride gas, when exists in the system, can be detected by the discoloration of the detecting agent. In the case where the detecting agent is used for the detection of the breakthrough of a hydride gas, the agent is used in a state that it is packed on the downstream side of a purifying agent layer inside a purifying column or packed among a plurality of purifying agent layers inside a column or packed in a separate detecting cylinder which is connected to the downstream side of a purifying column.

As described hereinbefore, the detecting agent is imparted with excellent characteristics as summarized in the following items (1) and (2).

① It can be used for detecting hydride gases in common with each other that are employed in a semiconductor manufacturing process, etc., and assures a high sensitivity and high discoloring rate.

② It is not discolored by a gas other than hydrides gases, such as hydrogen, nitrogen, air or the like and accordingly, it can independently detect a hydride gas in high accuracy and selectivity.

In the following, the present invention will be described in more detail with reference to the working examples, which however shall not construed to limit the invention thereto.

EXAMPLE 1 to 6

<Preparation of the detecting agnet>

A granular silica-gel as an inorganic carrier in an amount of 100 g which had a particle size of 5 to 10 mesh, a specific surface area of 325 $m^2/g$, a micropore volume of 0.99 mL (milliliter)/g an average micropore diameter of 0.99 Å, a bulk density of 0.420 g/mL (produced by Fuji Silicia Co., Ltd., under the trademark "Carriact-10") was impregnated with a solution of discoloring components composed of 1.0 g of molybdophosphoric acid hydrate and 0.2 g of cupric sulfate pentahydrate (ratio by weight of carrier:Mo:Cu= 1:0.0013:0.00049) in 270 mL of water, and thereafter the impregnated product was dried at $75°$ C. to prepare a detecting agent.

<Confirmation of non-discoloration due to other gas>

First of all, a confirmation test was carried out as a blank test to see whether or not an ordinary gas (hydrogen, nitrogen, air, etc.) exerts influence on the discoloration of the discoloring agent in the following manner.

Glass tubes of 19 mm in inside diameter each packed inside with 2.0 g of the above-prepared detecting agent were prepared in triplicate, and 100% by volume of hydrogen, 100% by volume of nitrogen and air were each passed through any one of the above-prepared glass tubes at a linear space velocity of 6.4 cm/sec to bring the gases into contact with the detecting agent. As a result, it was confirmed that the agent is not discolored by any of the gases. The results are given in Table 1.

TABLE 1

| Kind of gas | Gas through-flow time (Hr) | Discoloration |
| --- | --- | --- |
| Hydrogen | 120 | none |
| Nitrogen | 120 | none |
| Air | 120 | none |

Determination of detecting capability

Subsequently, a discoloration test was carried out in the following manner.

Nitrogen gases each containing a hydride gas at a prescribed concentration as shown in Table 2 were each passed through a glass tube of 19 mm in inside diameter which had been packed inside with 2.0 g of the above-prepared detecting agent at a linear space velocity of 6.4 cm/sec to bring each of the gases into contact with the detecting agent. Thus a measurement was made of the period of time taken for the discoloration of the detecting agent to be confirmed. The result are given in Table 2.

EXAMPLE 7

100 g of granular silica-gel same as that in Example 1 was impregnated with a solution of a discoloring component composed of 1.0 g of molybdophosphoric acid hydrate in 270 mL of water (ratio by weight of the carrier:Mo= 1:0.0013), and then the impregnated product was dried at 75° C. to prepare a detecting agent.

Subsequently nitrogen gas containing 0.05 ppm of arsine as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 2.

EXAMPLE 8

100 g of granular silica-gel same as that in Example 1 was impregnated with a solution of discoloring components composed of 1.0 g of molybdephosphoric acid hydrate and 0.4 g of cupric sulfate pentahydrate in 270 mL of water (ratio by weight of the carrier:Mo:Cu=1:0.0013:0.00098) and then the impregnated product was dried at 75° C. to prepare a detecting agent.

Subsequently nitrogen gas containing 0.05 ppm of arsine as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 2.

TABLE 2

| Example No. | Kind of hydride gas | Hydride gas. Concentration (ppm) | Time taken for discoloration (min) |
| --- | --- | --- | --- |
| 1 | Arsine | 0.5 | 0.5 |
| 2 | Arsine | 0.05 | 2 |
| 3 | Phosphine | 3.0 | 15 |
| 4 | Phosphine | 0.3 | 11 |
| 5 | Silane | 500 | 2 |
| 6 | Silane | 50 | 30 |
| 7 | Arsine | 0.05 | 15 |
| 8 | Arsine | 0.05 | 2 |

EXAMPLE 9

100 g of granular silica-gel same as that in Example 1 was impregnated with a solution of discoloring component composed of 0.5 g of molybdic acid monohydrate in 270 mL of water (ratio by weight of the carrier:Mo=1:0.0029), and then the impregnated product was dried at 75° C. to prepare a detecting agent.

Subsequently nitrogen gas containing 0.5 ppm of arsine as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 3.

EXAMPLE 10

100 g of granular silica-gel same as that in Example 1 was impregnated with a solution of discoloring components composed of 0.5 g of molybdic acid monohydrate and 0.25 g of cupric chloride pentahydrate in 270 mL of water (ratio by weight of the carrier:Mo:Cu=1:0.0029:0.0012), and then the impregnated product was dried at 75° C. to prepare a detecting agent.

Subsequently nitrogen gas containing 0.05 ppm of arsine as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 3.

EXAMPLE 11

100 g of granular silica-gel same as that in Example 1 was impregnated with a solution of discoloring components composed of 1.0 g of molybdic acid monohydrate and 0.2 g of cupric sulfate pentahydrate in 270 mL of water (ratio by weight of the carrier:Mo:Cu=1:0.0059:0.0005) and then the impregnated product was dried at 75° C. to prepare a detecting agent.

Sebsequently nitrogen gas containing 1000 ppm of silane as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 3.

EXAMPLE 12

100 g of granular silica-gel same as that in Example 1 was impregnated with a solution of discoloring components composed of 1.0 g of ammonium molybdate tetrahydrate and 0.2 g of cupric sulfate pentahydrate in 270 mL of water (ratio by weight of the carrier:Mo:Cu=1:0.0054:0.0005), and then the impregnated product was dried at 75° C. to prepare a detecting agent.

Subsequently nitrogen gas containing 1000 ppm of silane as a hydride gas was passed through a glass tube of 19 mm in inside diameter which had been packed inside with 2.0 g of the above-prepared detecting agent at a linear space velocity of 6.4 cm/sec to bring the gas into contact with the detecting agent. Thus a measurement was made of the period of time taken for the discoloration of the detecting agent to be confirmed. The result are given in Table 3.

TABLE 3

| Example No. | Reagent as detecting agent | Kind of hydride gas | Hydride gas. Concentration (ppm) | Time taken for discoloration (min) |
| --- | --- | --- | --- | --- |
| 9 | $MoO_3 \cdot H_2O$ | Arsine | 0.5 | 3 |
| 10 | $MoO_3 \cdot H_2O + CuCl_2$ | Arsine | 0.05 | 10 |
| 11 | $MoO_3 \cdot H_2O + CuSO_4$ | Silane | 1000 | 10 |
| 12 | $(NH_4)_6Mo_7O_{24} + CuSO_4$ | Silane | 1000 | 2 |

What is claimed is:

1. An agent for detecting a hydride gas which consists essentially of a discoloring component supported on an inorganic carrier, the discoloring component consisting essentially of (i) at least one member selected from the group consisting of a molybdenum-containing acid and a salt thereof and (ii) a cupric salt.

2. The agent for detecting a hydride gas according to claim 1 wherein the hydride gas is at least one member selected from the group consisting of arsine, phosphine, silane, diborane and selenium hydride.

3. The agent for detecting a hydride gas according to claim 1 wherein the molybdenum-containing acid is molybdophosphoric acid.

4. The agent for detecting a hydride gas according to claim 1 wherein the salt of a molybdenum-containing acid is at least one member selected from the group consisting of a sodium salt of molybdophosphoric acid, a potassium salt of molybdophosphoric acid and an ammonium salt of molybdophosphoric acid.

5. The agent for detecting a hydride gas according to claim 1 wherein the discoloring component comprises said salt of a molybdenum-containing acid, which is at least one salt of molybdic acid selected from the group consisting of sodium molybdate, potassium molybdate and ammonium molybdate.

6. The agent for detecting a hydride gas according to claim 1 wherein the cupric salt is at least one member selected from the group consisting of cupric nitrate, cupric sulfate, cupric chloride, cupric bromide and cupric acetate.

7. The agent for detecting a hydride gas according to claim 1 wherein the molybdenum-containing acid is molybdic acid.

8. The agent for detecting a hydride gas according to claim 1 wherein the molybdenum-containing acid is selected from the group consisting of molydosilicic acid and molybdoboric acid.

9. The agent for detecting a hydride gas according to claim 1 wherein the inorganic carrier is at least one member selected from the group consisting of silica, alumina, silica-alumina and zirconia.

10. The agent for detecting a hydride gas according to claim 9 wherein the inorganic carrier is white-to-colorless and has a specific surface area in the range of 50 to 500 $m^2/g$.

11. The agent for detecting a hydride gas according to claim 1 wherein the amounts of (i) the molybdenum-containing acid or a salt thereof and (ii) the cupric salt supported on the carrier are 1:0.00001 to 0.1:0.00001 to 0.05 expressed in terms of a ratio by weight of the inorganic carrier:metallic molybdenum in the discoloring component:metallic copper in the discoloring component.

12. The agent for detecting a hydride gas according to claim 11 wherein the ratio is 1:0.0002 to 0.02:0.0001 to 0.005.

13. An agent for detecting a hydride gas comprising:

(a) a discoloring component comprising (i) a molybdenum-containing acid or salt thereof selected from the group consisting of molybdic acid, molybdophosphoric acid, a sodium salt of molybdophosphoric acid, a potassium salt of molydophosphoric acid, an ammonium salt of molybdophosphoric acid, sodium molybdate, potassium molybdate and ammonium molybdate, and (ii) a cupric salt selected from the group consisting of cupric nitrate, cupric sulfate, cupric chloride, cupric bromide and cupric acetate, and (b) an inorganic carrier which supports said discoloring component, said inorganic carrier being selected from the group consisting of silica, alumina, silica-alumina and zirconia, wherein a ratio by weight of said molybdenum-containing acid or salt thereof, said cupric salt and said inorganic carrier is 1:00001 to 0.1:0.00001 to 0.05, expressed in terms of the weight of the inorganic carrier:metallic molybdenum in the discoloring component:metallic copper in the discoloring component.

14. The agent for detecting a hydride gas according to claim 13 wherein the ratio is 1:0002 to 0.02:0.0001 to 0.005.

15. The agent for detecting a hydride gas according to claim 14 wherein the inorganic carrier has a specific surface area of 50 to 500$m^2/g$.

* * * * *